United States Patent
Perry et al.

(10) Patent No.: US 9,221,012 B2
(45) Date of Patent: Dec. 29, 2015

(54) CARBON DIOXIDE ABSORBENT AND METHOD OF USING THE SAME

(71) Applicant: General Electric Company, Schenectady, NY (US)

(72) Inventors: Robert James Perry, Niskayuna, NY (US); Michael Joseph O'Brien, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 159 days.

(21) Appl. No.: 14/153,548

(22) Filed: Jan. 13, 2014

(65) Prior Publication Data

US 2014/0127105 A1 May 8, 2014

Related U.S. Application Data

(62) Division of application No. 12/817,276, filed on Jun. 17, 2010, now Pat. No. 8,747,694.

(51) Int. Cl.

| | |
|---|---|
| B01D 47/00 | (2006.01) |
| B01D 53/62 | (2006.01) |
| B01D 53/14 | (2006.01) |
| C07F 7/08 | (2006.01) |
| C10K 1/16 | (2006.01) |
| C10L 3/10 | (2006.01) |

(52) U.S. Cl.
CPC ............... *B01D 53/62* (2013.01); *B01D 47/00* (2013.01); *B01D 53/1475* (2013.01); *B01D 53/1493* (2013.01); *C07F 7/0854* (2013.01); *C10K 1/16* (2013.01); *C10L 3/104* (2013.01); *B01D 2252/205* (2013.01); *B01D 2252/20415* (2013.01); *B01D 2258/0283* (2013.01); *Y02C 10/04* (2013.01); *Y02C 10/06* (2013.01)

(58) Field of Classification Search
CPC ...................................................... B01D 47/00
USPC ................................................... 95/149, 236
See application file for complete search history.

(56) References Cited

U.S. PATENT DOCUMENTS

| | | | |
|---|---|---|---|
| 3,274,155 A * | 9/1966 | Caldwell et al. | 528/26 |
| 6,547,854 B1 | 4/2003 | Gray et al. | |
| 7,208,605 B2 | 4/2007 | Davis, Jr. | |
| 7,678,351 B2 | 3/2010 | Iyer et al. | |
| 8,500,887 B2 * | 8/2013 | Yeganeh et al. | 96/146 |
| 2007/0149398 A1 | 6/2007 | Jones et al. | |
| 2008/0226526 A1 | 9/2008 | Ronning et al. | |
| 2008/0282887 A1 | 11/2008 | Chance et al. | |
| 2008/0293976 A1 | 11/2008 | Olah et al. | |
| 2010/0021362 A1 | 1/2010 | Hunwick | |

FOREIGN PATENT DOCUMENTS

EP 0674936 B1 11/1998

OTHER PUBLICATIONS

Annual Energy Outlook 2008 With Projections to 2030; Date : Jun. 2008; URL: www.eia.doe.gov/oiaf/aeo/; 224 Pages.
Se-Na Kim, Won-Jin Son, Jung-Sik Choi and Wha-Seung Ahn; Abstract : CO2 adsorption using aminefunctionalized mesoporous silica prepared via anionic surfactantmediated synthesis; Microporous and Mesoporous Materials vol. 115, Issue 3, Nov. 1, 2008.
V.V. Guliants, M.A. Carreon, Y.S. Lin; Ordered mesoporous and macroporous inorganic films and membranes; Science Direct; Journal of Membrane Science 235 (2004) 53-72.
Ravikrishna Chatti, Amit K. Bansiwal, Jayashri, A. Thote, Vivek Kumar, Pravin Jadhav, Satish, K. Lokhande, Rajesh B. Biniwale, Nitin K. Labhsetwar and Sadhana S. Rayalu; Abstract : Amine loaded zeolites for carbon dioxide capture: Amine loading and adsorption studies; Science Direct, Microporous and Mesoporous Materials, vol. 121, Issues 1-3, May 1, 2009.

* cited by examiner

*Primary Examiner* — Robert A Hopkins
(74) *Attorney, Agent, or Firm* — Francis T. Coppa

(57) ABSTRACT

In accordance with one aspect, the present invention provides a composition which contains the amino-siloxane structures I, or III, as described herein. The composition is useful for the capture of carbon dioxide from process streams. In addition, the present invention provides methods of preparing the amino-siloxane composition. Another aspect of the present invention provides methods for reducing the amount of carbon dioxide in a process stream employing the amino-siloxane compositions of the invention, as species which react with carbon dioxide to form an adduct with carbon dioxide.

6 Claims, No Drawings

CARBON DIOXIDE ABSORBENT AND METHOD OF USING THE SAME

This application is a Divisional application of Ser. No. 12/817,276, filed on Jun. 17, 2010, the contents of which are incorporated herein by reference.

STATEMENT REGARDING FEDERALLY SPONSORED RESEARCH & DEVELOPMENT

This invention was made with Government support under grant number DE-NT0005310 awarded by the Department of Energy-NETL. The Government has certain rights in the invention.

BACKGROUND

The invention relates to amino-siloxane compositions and their use as carbon dioxide absorbent materials.

Pulverized coal power plants currently produce over half the electricity used in the United States. In 2007, these plants emitted over 1900 million metric tons of carbon dioxide ($CO_2$), and as such, accounted for 83% of the total $CO_2$ emissions from electric power generating plants and 33% of the total U.S. $CO_2$ emissions. Eliminating, or even reducing these emissions, will be essential in any plan to reduce greenhouse gas emissions.

Separating $CO_2$ from gas streams has been commercialized for decades in food production, natural gas sweetening, and other processes. Aqueous monoethanolamine (MEA) based solvent capture is currently considered to be the best commercially available technology to separate $CO_2$ from exhaust gases, and is the benchmark against which future developments in this area will be evaluated. Unfortunately, amine-based systems were not designed for processing the large volumes of flue gas produced by a pulverized coal power plant. Scaling the amine-based $CO_2$ capture system to the size required for such plants is estimated to result in an 83% increase in the overall cost of electricity from such a plant. Applying this technology to all existing pulverized coal power plants in the U.S. could cost $125 billion per year, making MEA-based $CO_2$ capture an undesirable choice for large-scale commercialization.

There are many properties that desirably would be exhibited, or enhanced, in any $CO_2$ capture technology contemplated to be a feasible alternative to the currently utilized MEA-based systems. For example, any such technology would desirably exhibit a high net $CO_2$ capacity and elimination of the carrier solvent (for example water), and could provide lower capital and operating costs (less material volume required to heat and cool, therefore less energy required). A lower heat of reaction would mean that less energy would be required to release the $CO_2$ from the material. Desirably, the technology would not require a pre-capture gas compression, so that a high net $CO_2$ capacity could be achieved at low $CO_2$ partial pressures, lowering the energy required for capture. Technologies utilizing materials with lower viscosities would provide improved mass transfer, reducing the size of equipment needed, as well as a reduction in the cost of energy to run it. Low volatility and high thermal, chemical and hydrolytic stability of the material(s) employed could reduce the amount of material needing to be replenished. Of course, any such technology would also desirably have low material costs, so that material make-up costs for the system would be minimized. The operability of $CO_2$ release at high pressures could reduce the energy required for $CO_2$ compression prior to sequestration. Finally, such technologies would also desirably exhibit reduced corrosivity to help reduce capital and maintenance costs, and further would not require significant cooling to achieve the desired net $CO_2$ loading, reducing operating costs.

Unfortunately, many of the above delineated desired properties interact and/or depend on one another, so that they cannot be varied independently. Trade-offs are therefore required. For example, in order to have low volatility, the materials used in any such technology typically must have a relatively high molecular weight. However, in order to achieve low viscosity, the materials must typically have a relatively low molecular weight. Moreover, in order to achieve high $CO_2$ capacity at low pressures, the overall heat of reaction of the absorbent material with carbon dioxide (to form an adduct comprising structural units derived from the absorbent material and $CO_2$) should be relatively high. However, the ease of regeneration of the absorbent material and carbon dioxide from the adduct would benefit from a relatively low heat of reaction.

Therefore there is a need for a $CO_2$ capture technology that optimizes as many of the above desired properties as possible, without causing substantial detriment to other desired properties. At a minimum, in order to be commercially viable, such technology would desirably be utilized at a relatively low cost, and would also utilize materials(s) having low volatility, high thermal stability, and a high net capacity for $CO_2$.

BRIEF DESCRIPTION

In accordance with one aspect, the present invention provides an amino-siloxane composition comprising structure I

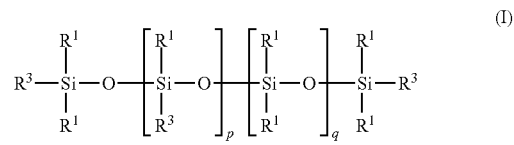

(I)

wherein $R^1$ is independently at each occurrence $C_1$-$C_5$ alkyl; $R^3$ is independently at each occurrence $R^1$ or $R^4$, wherein $R^4$ comprises structure II

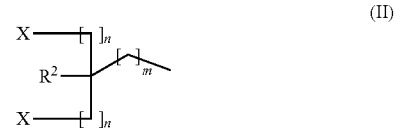

(II)

and wherein $R^2$ is independently at each occurrence hydrogen or a $C_1$-$C_{10}$ aliphatic radical; X is independently at each occurrence a $NH_2$ group or a cyano group; m is independently at each occurrence an integer from 1-5; n is independently at each occurrence an integer from 0-5; and m is independently at each occurrence an integer from 1-5; p is an integer from 0-100 and q is an integer from 0-500, with the proviso that at least one of $R^3$ is $R^4$.

In another aspect, the present invention provides an amino-siloxane composition comprising structure III

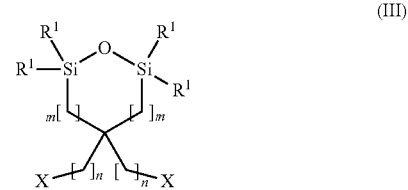

(III)

wherein $R^1$ is independently at each occurrence $C_1$-$C_5$ alkyl; X is independently at each occurrence a $NH_2$ group or a cyano group; n is independently at each occurrence an integer from 0-5 and m is independently at each occurrence an integer from 1-5.

In another aspect, the present invention provides a method of reducing the amount of carbon dioxide in a process stream, comprising the step of contacting the stream with a carbon dioxide absorbent comprising at least one amino-siloxane compound selected from the group consisting of amino-siloxanes having structure I and amino-siloxanes having structure III,

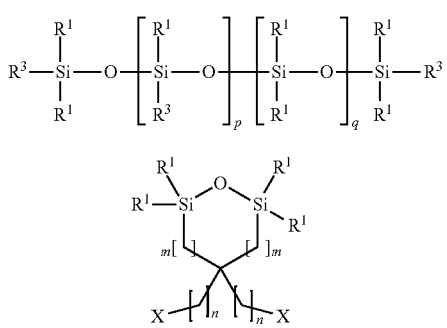

wherein $R^1$ is independently at each occurrence $C_1$-$C_5$ alkyl; $R^3$ is independently at each occurrence $R^1$ or $R^4$, wherein $R^4$ comprises structure II

and wherein $R^2$ is independently at each occurrence hydrogen or a $C_1$-$C_{10}$ aliphatic radical; X is independently at each occurrence a $NH_2$ group or a cyano group; m is independently at each occurrence an integer from 1-5; n is independently at each occurrence an integer from 0-5; p is an integer from 0-100 and q is an integer from 0-500; with the proviso that at least one of $R^3$ is $R^4$.

DETAILED DESCRIPTION

In the following specification and the claims, reference will be made to a number of terms, which shall be defined to have the following meanings. Unless defined otherwise, technical and scientific terms used herein have the same meaning as is commonly understood by one of skill in the art to which this invention belongs.

The terms "first", "second", and the like, as used herein do not denote any order, quantity, or importance, but rather are used to distinguish one element from another. Also, the terms the terms "front", "back", "bottom", and/or "top", unless otherwise noted, are merely used for convenience of description, and are not limited to any one position or spatial orientation. If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity). Similarly, "free" may be used in combination with a term, and may include an insubstantial number, or trace amounts, while still being considered free of the modified term. Here and throughout the specification and claims, range limitations may be combined and/or interchanged. Such ranges are identified and include all the sub-ranges contained therein, unless context or language indicates otherwise.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "solvent" can refer to a single solvent or a mixture of solvents.

As used herein the term "aliphatic radical" refers to an organic radical having a valence of at least 1, including a linear or branched array of atoms, which is not cyclic. Aliphatic radicals are defined to comprise at least one carbon atom. The array of atoms comprising the aliphatic radical may include heteroatoms such as nitrogen, sulfur, silicon, selenium and oxygen, or may be composed exclusively of carbon and hydrogen. For convenience, the term "aliphatic radical" is defined herein to encompass, as part of the "linear or branched array of atoms which is not cyclic", a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —$CH_2CHBrCH_2$—), and the like. Further examples of aliphatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e., —CHO), hexyl, hexamethylene, hydroxymethyl (i.e., —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., $(CH_3)_3Si$—), t-butyldimethylsilyl, 3-trimethyoxysilylpropyl (i.e., $(CH_3O)_3SiCH_2CH_2CH_2$—), vinyl, vinylidene, and the like. By way of further example, a $C_1$-$C_{10}$ aliphatic radical contains at least one, but no more than 10, carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical.

As noted herein, in one embodiment, the present invention provides an amino-siloxane composition comprising structure I

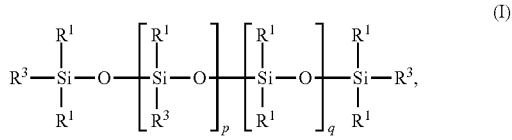

wherein $R^1$ is independently at each occurrence $C_1$-$C_5$ alkyl; $R^3$ is independently at each occurrence $R^1$ or $R^4$, wherein $R^4$ comprises structure II

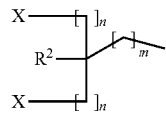

and wherein $R^2$ is independently at each occurrence hydrogen or a $C_1$-$C_{10}$ aliphatic radical; X is independently at each occurrence a $NH_2$ group or a cyano group; m is independently at each occurrence an integer from 1-5; n is independently at each occurrence an integer from 0-5; and m is independently at each occurrence an integer from 1-5; p is an integer from 0-100, and q is an integer from 0-500, with the proviso that at least one of $R^3$ is $R^4$. In one embodiment, the amino-siloxane having structure I includes nitrogen in an amount of at least about 1.3%. In another embodiment, the amino-siloxane having structure I includes nitrogen in an amount of at least about 3.2%. In yet another embodiment, the amino-siloxane having structure I includes nitrogen in an amount of at least about 6.4%. Amino-siloxane compositions having structure I are illustrated in Table 1 below.

TABLE 1

Examples of Amino-Siloxane Compositions Having Structure 1

| Entry | Structure | $R^1$ | $R^2$ | n | m | X | p | q |
|---|---|---|---|---|---|---|---|---|
| Ia | 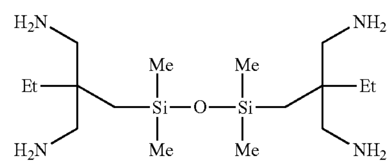 | Me | Et | 1 | 1 | $NH_2$ | 0 | 0 |
| Ib | 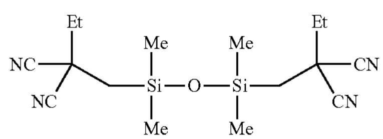 | Me | Et | 0 | 1 | $NH_2$ | 0 | 0 |
| Ic | 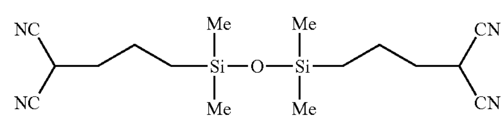 | Me | H | 1 | 3 | CN | 0 | 0 |
| Id | 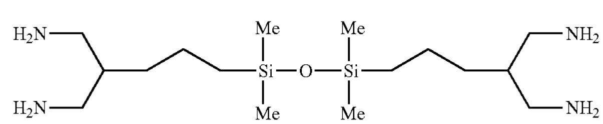 | Me | H | 1 | 3 | $NH_2$ | 0 | 0 |
| Ie | 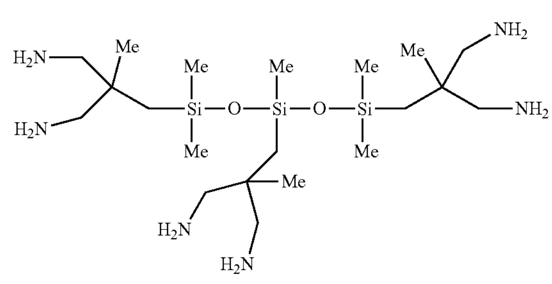 | Me | Me | 1 | 1 | $NH_2$ | 1 | 0 |
| If | 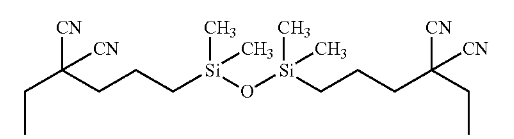 | Me | Et | 0 | 3 | CN | 0 | 0 |
| Ig | 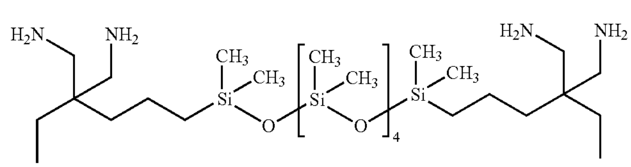 | Me | Et | 1 | 2 | $NH_2$ | 0 | 4 |

TABLE 1-continued

Examples of Amino-Siloxane Compositions Having Structure 1

| Entry | Structure | R¹ | R² | n | m | X | p | q |
|---|---|---|---|---|---|---|---|---|
| Ih | 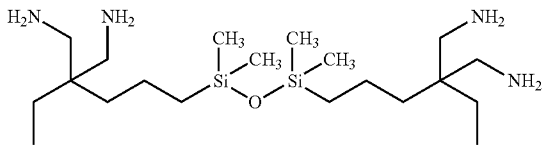 | Me | Et | 1 | 2 | NH₂ | 0 | 0 |
| Ij | 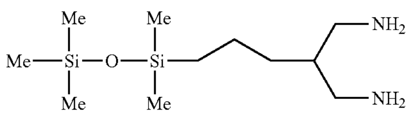 | Me | H | 1 | 3 | NH₂ | 0 | 0 |
| Ik | 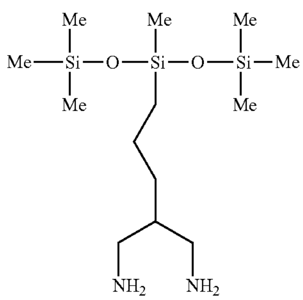 | Me | H | 1 | 3 | NH₂ | 1 | 0 |

In one embodiment, the amino-siloxane has structure Ia.

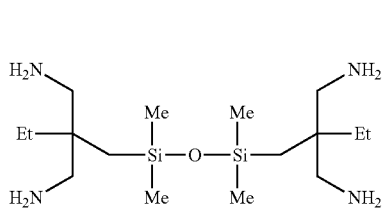

(Ia)

In another embodiment, the amino-siloxane has structure Ib.

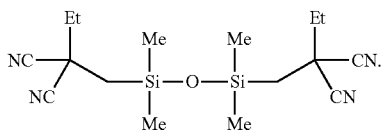

(Ib)

In another embodiment, the amino-siloxane has structure Ic

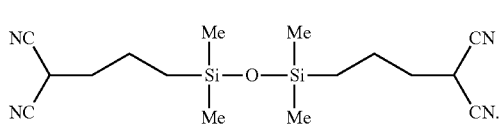

(Ic)

In another embodiment, the amino-siloxane has structure Ie

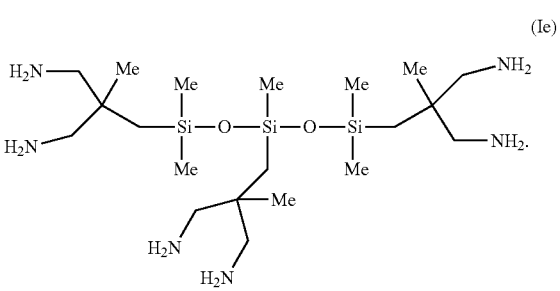 [SMILES: CC(CN)(CN)C[Si](C)(C)O[Si](C)(CC(C)(CN)CN)O[Si](C)(C)CC(C)(CN)CN]

(Ie)

In one embodiment, the present invention provides an amino-siloxane composition comprising structure III

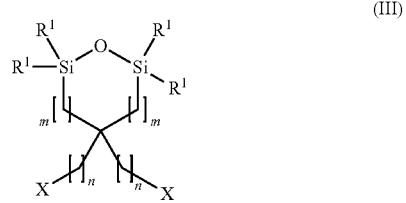

(III)

wherein $R^1$ is independently at each occurrence $C_1$-$C_5$ alkyl; X is independently at each occurrence an $NH_2$ group or a cyano group; n is independently at each occurrence an integer from 0-5, and m is independently at each occurrence an integer from 1-5. Amino-siloxane compositions having structure III are illustrated in Table 2 below.

TABLE 2

Examples of Amino-Siloxane Compositions Having Structure III

| Entry | Structure | $R^1$ | m | n | X |
|---|---|---|---|---|---|
| 2a | Me₂Si-O-SiMe₂ ring with C(CN)₂ | Me | 1 | 0 | CN |
| 2b | Me₂Si-O-SiMe₂ ring with C(CH₂NH₂)₂ | Me | 1 | 1 | NH₂ |
| 2c | Me₂Si-O-SiMe₂ 7-membered ring with C(CN)₂ | Me | 3 | 0 | CN |
| 2d | Et₂Si-O-SiEt₂ ring with C(CH₂CH₂NH₂)₂ | Et | 2, 1 | 2 | NH₂ |

In one embodiment, the amino-siloxane composition has structure IIIa.

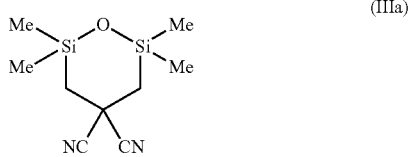 [SMILES: C[Si]1(C)CC(C#N)(C#N)C[Si](C)(C)O1]

(IIIa)

In another embodiment, the amino-siloxane composition has structure IIIb.

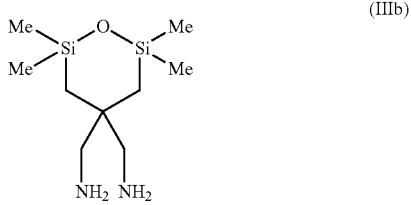 [SMILES: C[Si]1(C)CC(CN)(CN)C[Si](C)(C)O1]

(IIIb)

In one embodiment, the present invention relates to amino-siloxane carbon dioxide absorbents and methods of using the absorbents to absorb carbon dioxide from process streams, e.g., as may be produced by methods of generating electricity.

Conventional carbon dioxide absorbents lack one or more of the properties considered important, if not critical, to commercial feasibility of their use in many technologies. MEA-based aqueous absorbents, for example, may not be suited for use with large volumes of $CO_2$-containing exhaust gases. As a result, the use of MEA-based absorbents under such circumstances may be prohibitively energy intensive and costly for implementation.

In one embodiment, the present invention provides amino-siloxanes useful as carbon dioxide absorbents which are liquids under ambient conditions, and which remain liquids following exposure to carbon dioxide. In one embodiment, the present invention provides a liquid amino-siloxane having structure I, which reacts with carbon dioxide to form a reaction product referred to as an adduct of the amino-siloxane with carbon dioxide, the adduct also being a liquid under ambient conditions. In another embodiment, the adduct may be a solid under ambient conditions. In another embodiment, the amino-siloxane composition having structure II reacts with carbon dioxide to form a reaction product or an adduct of the amino-siloxane with carbon dioxide, the adduct also being a liquid under ambient conditions. In certain embodiments, the physical state of the adduct of the amino-siloxane composition with $CO_2$ can be controlled by limiting the degree to which the amino-siloxane composition has been fully reacted with $CO_2$. For example, it may be possible and advantageous to limit the time and conditions of contacting the amino-siloxane composition with $CO_2$, such that the adduct contains less than the theoretical amount of $CO_2$ derived structural units (i.e. carbamate groups). Those skilled in the art will appreciate that a primary or secondary amine reacts with carbon dioxide to form an ammonium carbamate. In one embodiment, an amino-siloxane composition, which when fully reacted with $CO_2$ is a solid under ambient conditions, can be maintained in the liquid state when only partially reacted with $CO_2$. In one embodiment, the present invention provides a reaction product of an amino-siloxane composition with $CO_2$, in which less than the theoretical amount of $CO_2$ has reacted with the reactive groups of the amino-siloxane composition. In one embodiment, the degree of reaction with $CO_2$ is in a range from about 10 percent of theoretical to about 100 percent of theoretical. In an alternate embodiment, the degree of reaction with $CO_2$ is in a range from about 20 percent of theoretical to about 70 percent of theoretical. In yet another embodiment, the degree of reaction with $CO_2$ is in a range from about 30 percent of theoretical to about 50 percent of theoretical.

The amino-siloxane composition undergoing the reaction with $CO_2$ to form a reaction product may be an essentially pure amino-siloxane, or may be a mixture of an amino-siloxane with one or more other components, for example water or other diluents such as triethylene glycol. Typically, the amino-siloxane compositions are capable of absorbing an amount of $CO_2$ corresponding to from about 1 to about 50 percent by weight of the composition. In one embodiment, the amino-siloxane compositions provided by the present invention and/or used according to the methods provided by the present invention, may be non-oligomeric and/or non-polymeric, in that the materials do not contain "adjacent repeat units" derived from monomeric units. As used herein, an adjacent repeat unit derived from a monomeric unit is a structural unit derived from a monomer and present in a molecule chemically bound to an identical structural unit in the same molecule without an intervening structure disposed between the two. Oligomeric materials are defined herein as molecules having between two to twenty adjacent repeat units, and polymeric materials are defined herein as molecules having more than twenty adjacent repeat units. Notwithstanding the relatively low molecular weight of the amino-siloxane compositions provided by the present invention when compared to analogous oligomeric and polymeric materials, the amino-siloxane compositions provided by the present invention typically exhibit a low vapor pressure. They usually also comprise functional groups (e.g. $NH_2$ groups, secondary amine groups) that either react reversibly with, or have a high affinity for, $CO_2$. In another embodiment, the amino-siloxane compositions provided by the present invention and/or used according to the methods provided by the present invention, may be oligomeric and/or polymeric.

Amino-siloxane compositions provided by the present invention may exhibit properties which are important for the reversible capture of carbon dioxide. Thus, amino-siloxane compositions provided by the present invention in various embodiments remain in a liquid state over a range of temperatures, are relatively non-volatile when compared to MEA, are thermally stable, and do not require a carrier fluid. Further, the amino-siloxane compositions provided by the present invention may exhibit a high capacity for $CO_2$ absorption. The amino-siloxane compositions provided by the present invention, owing to the presence of siloxane groups, are in various embodiments relatively hydrophobic, compared to MEA-based absorbents, and may be employed under nonaqueous conditions.

As noted, the amino-siloxane compositions provided by the present invention are relatively non-volatile liquids at room temperature, and may be stable at high temperatures, e.g., up to about 150° C., and typically may not require the use of additional solvents in order to achieve an acceptable viscosity level. As is amply disclosed in the Examples section of the present disclosure, the amino-siloxane compositions comprising functional groups which are reversibly reactive with carbon dioxide may be prepared efficiently and with a high level of structural diversity.

The amino-siloxane compositions provided by the present invention may desirably be functionalized with groups that enhance the net capacity of the compositions for $CO_2$ absorption. Functional groups that are expected to be $CO_2$-philic, and thus enhance the affinity of the amino-siloxane composition for $CO_2$, include acetate groups, carbonate groups, ketone groups, quaternary ammonium groups, imine groups, guanidine groups, and amidine groups. Examples of amine functional groups that exhibit $CO_2$-reactivity include primary amine groups and secondary amine groups. Numerous methods for the introduction of such functional groups are known to those of ordinary skill in the art using techniques such as hydrosilylation and displacement. Michael A. Brook's book, *Silicon in Organic, Organometallic, and Polymer Chemistry* (Wiley VCH Press, 2000), provides useful guidance in this area, and is incorporated herein by reference in its entirety for purposes related to synthetic methods. In one embodiment, the present invention provides amino-siloxane compositions comprising one or more guanidine groups or amidine groups. A primary amine group ($NH_2$) may be transformed into a guanidine group under mild conditions by reaction with the Vilsmeier salt of, for example, tetraisopropyl thiourea or diisopropyl carbodiimide, to provide a guanidine group. Similarly, amidine groups may be prepared by, for example, by reaction of a primary or secondary amine group with ethyl acetimidate (the Pinner reaction product of acetonitrile with ethanol).

Optionally, the amino-siloxane composition provided by the present invention may also include other components, such as oxidation inhibitors to increase oxidative stability, and anti-foaming agents. The use of oxidation inhibitors, also called antioxidants, can be especially advantageous in those embodiments of the invention wherein the amine groups are sensitive to oxidation.

In one embodiment, the present invention provides a method of reducing the amount of carbon dioxide in a process stream, comprising the step of contacting the stream with a carbon dioxide absorbent composition, comprising at least one amino-siloxane selected from the group consisting of amino-siloxanes having structure I, and amino-siloxanes having structure III

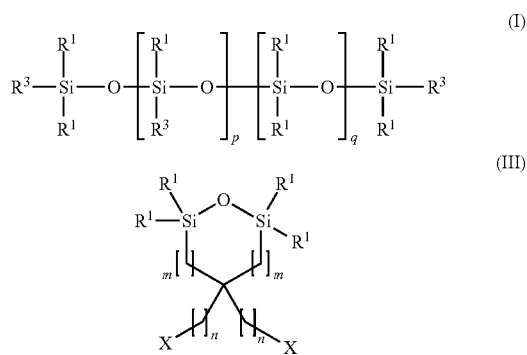

wherein $R^1$ is independently at each occurrence $C_1$-$C_5$ alkyl; $R^3$ is independently at each occurrence $R^1$ or $R^4$, wherein $R^4$ comprises structure II

and wherein $R^2$ is independently at each occurrence hydrogen or a $C_1$-$C_{10}$ aliphatic radical; X is independently at each occurrence an $NH_2$ group or a cyano group; m is independently at each occurrence an integer from 1-5; n is independently at each occurrence an integer from 0-5; p is an integer from 0-100, and q is an integer from 0-500; with the proviso that at least one of $R^3$ is $R^4$. In one embodiment, the present invention provides a reaction product of an amino-siloxane composition having structure I and/or II with carbon dioxide. The experimental section of this disclosure provides detailed guidance on the preparation of such reaction products, also referred to at times herein as adducts of the amino-siloxane composition with carbon dioxide.

In another embodiment, the present invention provides a method of reducing the amount of carbon dioxide in a process stream comprising contacting the stream with a carbon dioxide absorbent comprising at least one amino-siloxane having structures I and/or III. The carbon dioxide absorbents provided herein are expected to provide advantages when utilized to remove $CO_2$ from process gases, as compared to those currently commercially available and/or utilized for this purpose. As such, a method of reducing the carbon dioxide in a process stream is provided, and comprises contacting the process stream with the carbon dioxide absorbents described herein. The process stream so treated may be any wherein the level of $CO_2$ therein is desirably reduced, and in many processes, $CO_2$ is desirably reduced at least in the exhaust streams produced thereby. The process stream is typically gaseous, but may contain solid or liquid particulates, and may be at a wide range of temperatures and pressures, depending on the application. In one embodiment, the process stream may be a process stream from industries, such as chemical industries, cement industries, steel industries, flue gases from a power plant, and the like. In one embodiment, the process stream may be a fuel stream. In another embodiment, the fuel stream may be a natural gas stream or a syngas stream. In yet another embodiment, the process stream is selected from the group consisting of a combustion process, a gasification process, a landfill, a furnace, a steam generator, a boiler and combinations thereof.

The carbon dioxide absorbents, and methods of using them, provided herein may benefit from economies of scale which lower their cost. Further, the absorbents have relatively low volatility, high thermal stability, and can be provided using the synthetic methods disclosed herein. It is believed that the compositions provided by the present invention will be especially useful in power plants requiring means for reducing carbon dioxide emissions. Thus, in one embodiment, the present invention provides a method for reducing carbon dioxide emissions utilizing the compositions provided by the present invention.

EXAMPLES

The following examples illustrate methods and embodiments in accordance with the invention. Unless specified otherwise, all ingredients may be commercially available from such common chemical suppliers as Alpha Aesar, Inc. (Ward Hill, Mass.), Sigma Aldrich (St. Louis, Mo.), Spectrum Chemical Mfg. Corp. (Gardena, Calif.), and the like.

Carbon dioxide uptake measurements were carried out using lab scale techniques.

Representative Lab-Scale Example:

To a tared, 25 mL, 3-neck, round bottom flask equipped with a mechanical stirrer, gas inlet tube and a gas bubbler was placed a pre-determined weight of solvent (typically approximately 2 grams). The solvent was stirred and heated in an oil bath at 40° C. while a constant flow of dry $CO_2$ was passed into the flask. After 2 hours of exposure to $CO_2$, the gas was turned off, the reaction flask was weighed, and the weight recorded. The difference in weight was the amount of $CO_2$ that had been adsorbed, which can be expressed as a % weight gain from the original weight of the solvent.

Example 1

Preparation of Amino-Siloxane Composition (Ia)

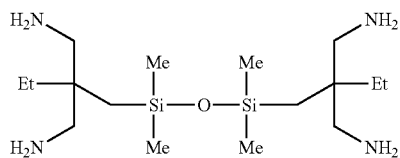 [SMILES: CCC(CN)(CN)C[Si](C)(C)O[Si](C)(C)CC(CC)(CN)CN]

A solution of 1,3-bis(2,2-dicyanobutyl)-1,1,3,3-tetramethyldisiloxane (2.45 g, 7.1 mmol) in diethylether (25 mL) was added slowly over a period of 15 min to a mechanically stirred, pre-cooled slurry of lithium aluminum hydride (2.49 g, 65.7 mmol) in diethylether (275 mL) at a temperature of about 0° C. under $N_2$, in order to maintain the temperature of the mixture below 5° C. The mixture was stirred for 6 hours, followed by addition of water (10 mL), 1 M NaOH (40 mL) and water (50 mL), in the given order, with vigorous stirring. This was followed by the addition of diethylether (100 mL). The reaction mixture was then extracted with additional portions of diethylether (4×100 mL). The diethylether layers were combined, dried with $Na_2SO_4$, filtered and concentrated to an oil. The aqueous layer was further extracted with $CHCl_3$ (3×30 mL), and treated, following the method described above. The crude products were combined; dissolved in diethylether, and acidified with concentrated HCl. This was followed by isolation of the salt as a white solid. The isolated solid was dissolved in water, neutralized with 1N NaOH, extracted with $CHCl_3$, dried with $Na_2SO_4$, and concentrated to give 1.02 g (40%) of the reaction product 1a as a colorless liquid.

The following data (e.g., spectroscopic data) were obtained for the product 1a:

$^1$H NMR ($CDCl_3$) δ: 2.39 (s, 8H), 1.14 (q, J=7.6 Hz, 8H), 1.08 (br s, 8H), 0.64 (t, J=7.6 Hz, 6H), 0.41 (s, 4H), −0.02 (s, 12H).

$^{13}$C {$^1$H}NMR ($CDCl_3$): 48.1, 41.0, 27.2, 23.6, 7.8, 3.0 ppm. FT-IR (neat): 3377, 3296, 2959, 2852, 1604, 1463, 1408, 1379, 1253, 1044, 836, 802, 750 cm$^{-1}$.

The exact mass (MS:) calculated for $C_{16}H_{43}N_4OSi_2$ (M+H$^+$) was 363.2975, observed (M+H$^+$): 363.2949.

Example 2

Preparation of Amino-Siloxane Composition (Ib)

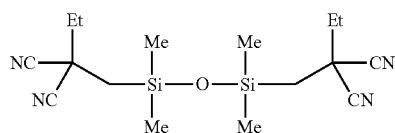 [SMILES: CCC(C#N)(C#N)C[Si](C)(C)O[Si](C)(C)CC(C#N)(C#N)CC]

To a solution of 2-ethylmalononitrile (2.0 g, 21.2 mmol) in tetrahydrofuran (THF, 10 mL) at 0° C. was added potassium t-butoxide (1.75 g, 15.6 mmol), to provide a clear brown solution. A solution of 1,3-bis(iodomethyl)1,1,3,3-tetramethyldisiloxane (2.93 g, 14.2 mmol) in THF (6 mL) was added drop-wise, using an addition funnel, when all the potassium t-butoxide had dissolved. On completion of the addition of the above solution, a fresh portion of THF (6 mL) was used to rinse the addition funnel. The reaction mixture was then allowed to warm to room temperature. As the reaction preceded, the solution lightened in color and solid-precipitated. At the end of three days, the reaction mixture was filtered, and the solids were washed with THF. The solution was concentrated on a rotary evaporator and the residue thus obtained was partitioned between chloroform and water. The organics combined and were washed with water, dilute sodium hydrosulfite, followed by water, and finally with saturated sodium chloride solution, followed by drying over anhydrous sodium sulfate. Following the wash, the solvent was removed under reduced pressure, yielding 2.67 g of crude material as a yellow oil. Purification of the crude product was carried out using column chromatography (200-400 mesh silica gel, 3.5:1 hexanes:ethyl acetate as eluent). The result was 1.48 g (60%) of reaction product 1b, obtained as a white solid. Further purification of the reaction product 1b was carried out, employing recrystallization with a heptane:acetone solvent mixture.

The following data (e.g., spectroscopic data) were obtained for the product 1b:

The melting point of the material was determined to be 39-41° C.

$^1$H NMR ($CDCl_3$) δ: 2.03 (q, J=8 Hz, 4H), 1.39 (s, 4H), 1.26 (t, J=8 Hz, 6H), 0.35 (s, 12H).

$^{13}C$ {$^1H$}NMR (CDCl$_3$): 116.61, 35.33, 33.96, 27.03, 9.94, 1.44 ppm. FT-IR (neat): 2982, 2944, 2885, 2245, 1580, 1462, 1410, 1392, 1329, 1311, 1256, 1239, 1116, 1082, 959, 935, 844, 809, 791 cm$^{-1}$.

The exact mass (MS): Calculated for C$_{16}$H$_{27}$N$_4$OSi$_2$ (M+H$^+$): 333.2757; observed (M+H$^+$): 333.2755.

Example 3

Preparation of Amino-Siloxane Composition (Ic)

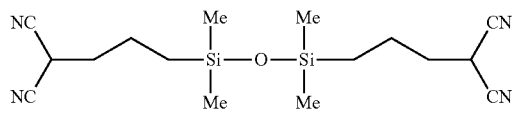 [SMILES: C[Si](C)(CCCC(C#N)C#N)O[Si](C)(C)CCCC(C#N)C#N]

To a solution of malononitrile (8.42 g, 127 mmols) in THF (35 mL) at 0° C., was added potassium t-butoxide (5.15 g, 45.9 mmols). The resulting milky pink solution was stirred under nitrogen for 15 minutes, followed by dropwise addition of 1,3-bis(3-iodopropyl)-1,1,3,3-tetramethyldisiloxane (10.0 g, 42.5 mmol) in THF (10 mL) over a period of 20 minutes, using an addition funnel. The addition funnel was rinsed using THF (5 mL). The reaction mixture was allowed to warm to room temperature and allowed to stay overnight. At the end of the stipulated time, the THF was removed using a rotary evaporator, and the residue was partitioned between chloroform and 10% HCl. The organics were then washed twice with deionized water and once each with dilute NaHSO$_3$, water, and saturated sodium chloride. Following the washing step, the organics were dried over anhydrous sodium sulfate, and the solvent was removed on a rotary evaporator to yield 7.2 g (98%) of the crude product as a red oil. Further purification of the crude product was carried out using column chromatography (200-400 mesh silica gel, 3:1 hexanes:ethyl acetate as eluent), to yield the reaction product 1c (6.26 g, 85% yield) as a light yellow oil.

The following data (e.g., spectroscopic data) were obtained for the product 1c:

1H NMR (CDCl3) δ: 3.78 (t, J=8 Hz, 2H), 2.04 (q, J=8 Hz, 4H), 1.63 (m, 4H), 0.57 (m, 4H), 0.09 (s, 12H).

13C{1H} NMR (CDCl3): 113.02, 33.67, 22.27, 20.66, 17.05, 0.27 ppm.

FT-IR (neat): 2958, 2923, 2882, 2258, 1578, 1460, 1412, 1349, 1314, 1260, 1180, 1066, 849, 798, 767, 706 cm−1.

The exact mass MS: calculated for C16H27N4OSi2 (M+H+): 347.1723, observed (M+H+): 347.1714.

Example 4

Preparation of Amino-Siloxane Composition (2a)

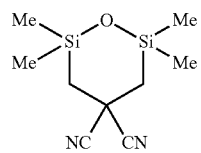

Preparation of 1,3-bis(iodomethyl)-1,1,3,3-tetramethyldisiloxane: 1,3-Bis(chloromethyl)-1,1,3,3-tetramethyldisiloxane (20.0 g, 173 mmols alkyl chloride) was combined with acetone (80 mL) and sodium iodide (39.0 g, 260 mmol). The reaction mixture was then heated to a temperature of about 35-40° C. overnight. At the end of the stipulated time the reaction mixture was cooled and filtered to remove any salts. The acetone was then removed using a rotary evaporator. The residue obtained, which was a mixture of solid and liquid, was then partitioned between heptane and water. The organic layer was washed with dilute sodium hydrosulfite, water, and saturated sodium chloride, and dried over anhydrous sodium sulfate. The solvent was removed on a rotary evaporator to yield the product compound 1,3-bis(iodomethyl)-1,1,3,3-tetramethyldisiloxane (30.3 g, 85%) as a colorless oil.

The following data (e.g., spectroscopic data) were obtained for product compound 1,3-bis(iodomethyl)-1,1,3,3-tetramethyldisiloxane:

$^1$H NMR (CDCl$_3$) δ: 2.01 (s, 4H), 0.28 (s, 12H).

$^{13}$C {$^1$H}NMR (CDCl$_3$): −0.29, −12.49.

Malononitrile (6.4 g, 97 mmol) in THF (35 mL) was cooled in an ice bath under nitrogen, followed by addition of solid potassium t-butoxide (5.4 g, 48 mmol), to yield a milky pink reaction mixture. After approximately 15 minutes, a solution of 1,3-bis(iodomethyl)1,1,3,3-tetramethyldisiloxane (10.0 g, 48 mmols alkyl iodide) in THF (10 mL) was added dropwise over a period of 10 minutes using an addition funnel. The addition funnel was then rinsed with THF (5 mL). The ice bath was removed and the reaction mixture was allowed to warm to room temperature and kept overnight. The reaction mixture turned from pink to orange. At this point, the reaction mixture was filtered to remove solids, and the solvent was removed under reduced pressure. The residue was dissolved in chloroform and washed with 5% NaOH, followed by deionized water (4×), and dried over anhydrous sodium sulfate. The solution was then filtered, and solvent was removed using a rotary evaporator. The crude solid product was then recrystallized twice from a mixture of cyclohexane and isopropanol (20 mL/2 mL to provide the reaction product 2a (3.6 g, 67% yield) as a white solid.

The following data (e.g., spectroscopic data) were obtained for the product 2a:

The melting point was determined to be 132-134° C.

$^1$H NMR (CDCl$_3$) δ: 1.46 (s, 4H) 0.32 (s, 12H).

$^{13}$C {$^1$H}NMR (CDCl$_3$): 118.08, 28.77, 26.42, 1.47.

FT-IR (neat): 2966, 2240, 1425, 1252, 1023, 1001, 968, 817, 762, 695 Cm$^{-1}$.

The exact mass MS: calculated for: C$_9$H$_{17}$N$_2$OSi$_2$ (M+H$^+$): 225.0879; observed (M+H$^+$): 225.0870.

Example 5

Preparation of Amino-Siloxane Compound (2b)

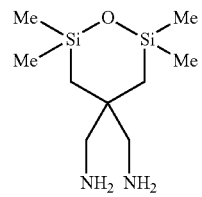

A solution of 2,2,6,6-tetramethyl-1,2,6-oxadisilinane-4,4-dicarbonitrile (3.4 g, 15.1 mmol) in THF/diethylether (20 mL/20 mL) was added slowly over a period of 25 min to a mechanically stirred, pre-cooled slurry of lithium aluminum hydride (2.7 g, 70 mmol) in diethylether at −5° C. under N$_2$. The temperature of the reaction mixture was maintained below 5° C. The reaction mixture was stirred for 2.5 h, followed by the addition of water (10 mL), 20% NaOH (20 mL), and additional water (40 mL) (in that sequence), with vigorous stirring. An additional amount of diethylether was added (50 mL), to form a two phase slurry. The diethylether was decanted from the 2-phase slurry, and a white sludge was extracted with {additional} diethylether (2×50 mL). The diethylether layers were combined, dried with MgSO$_4$, filtered, and concentrated to obtain a hazy white liquid which was fractionally distilled at 75-77° C./0.2 torr, to give 2.1 g (60%) reaction product 2b, as a colorless liquid.

The following data (e.g., spectroscopic data) were obtained for the product 2b:

$^1$H NMR (CDCl$_3$) δ: 2.70 (s, 4H); 1.93 (br s, 4H); 0.58 (s, 4H); 0.15 (s, 12H).

$^{13}$C {$^1$H} NMR (CDCl$_3$): 54.2, 40.7, 22.7, 2.7 ppm.

FT-IR (neat): 3385, 3305, 2961, 2899, 2869, 1603, 1460, 1417, 1314, 1259, 1189, 1058, 988, 853, 816, 761, 644, 601 cm$^{-1}$.

The exact mass MS: calculated for: C$_9$H$_{25}$N$_2$OSi$_2$ (M+H$^+$): 233.1505; observed (M+H$^+$): 233.1495.

Example 6

Preparation of Cyanosiloxane 1f

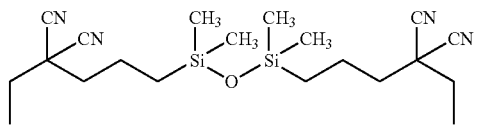 [SMILES: CCC(C#N)(C#N)CCC[Si](C)(C)O[Si](C)(C)CCCC(C#N)(C#N)CC]

To an ice cold solution of 2-ethylmalononitrile (4.5 g, 47.8 mmol) in THF (25 mL) was added potassium t-butoxide (4.3 g, 38.3 mmol). This caused the mixture to turn clear brown. Once all of the KOtBu had dissolved (10-15 minutes), a solution of 1,3-bis(iodopropyl)1,1,3,3-tetramethyldisiloxane (7.48 g, 31.8 mmol RI) in THF (8 mL) was added dropwise. On completion of the addition, the addition funnel was rinsed with another portion of fresh THF (3 mL). The reaction mixture was allowed to warm to room temperature for 2 hours. As the reaction proceeded, the color changed from clear brown to milky yellow. At the end of the stipulated time, the reaction mixture was filtered and the solids were washed with THF. The THF solution that resulted was then stripped under reduced pressure. The residue was then partitioned between chloroform and water. The organic phase was washed with water (two portions), followed by washing with dilute sodium hydrosulfite, and finally with saturated sodium chloride solution. The organic phase was dried over anhydrous potassium carbonate, and the chloroform was stripped off under reduced pressure. The crude product 1f obtained was purified using column chromatography (200-400 mesh silica gel, 3:1 heptane:ethyl acetate as eluent). The product 1f was obtained as a slightly yellow oil (5.38 g ~84%).

The following data (e.g., spectroscopic data) were obtained for the product 1f:

$^1$H NMR (CDCl$_3$) δ: 1.98 (q, J=8 Hz, 4H, C$\underline{H}_2$CH$_3$), 1.93 (m, 4H, CH$_2$—C(CN)$_2$), 1.69 (m, 4H, CH$_2$C$\underline{H}_2$CH$_2$), 1.26 (t, J=8 Hz, 6H, CH$_2$C$\underline{H}_3$), 0.61 (m, 4H, CH$_2$Si), 0.10 (s, 12H, CH$_3$—Si).

$^{13}$C {$^1$H}NMR (CDCl$_3$): 115.67, 40.54, 38.67, 31.59, 19.82, 17.74, 9.88, 0.34. FT-IR: 2979, 2957, 2884, 2247, 1461, 1412, 1303, 1255, 1193, 1063, 843, 801, 765 cm$^{-1}$.

Exact mass MS: Calc'd for: C$_{20}$H$_{35}$N$_4$OSi$_2$ (M+H$^+$); 403.2349. Found; 403.2362.

Example 7

Preparation of Aminosiloxane 1h

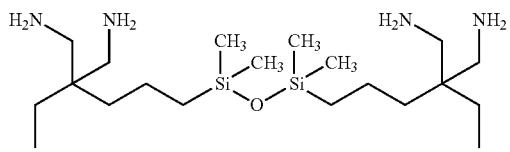 [SMILES: CCC(CN)(CN)CCC[Si](C)(C)O[Si](C)(C)CCCC(CC)(CN)CN]

To an ice cold mixture of lithium aluminum hydride (1.80 g, 47.4 mmols, 190 mmols H) in ether (100 mL) was added dropwise, under nitrogen, a solution of 1,3-bis(4,4-dicyanohexyl)-1,1,3,3-tetramethyldisiloxane 1f (3.16 g, 7.8 mmols, 31.4 mmols CN) in ether (50 mL). The reaction mixture was allowed to slowly warm to room temperature where it was kept for three hours. At the end of the stipulated time the reaction mixture was cooled back down to about 0° C., followed by addition of 10 mL of water over approximately 15 minutes and 50% sodium hydroxide 0.5 mL. The reaction mixture warmed to room temperature, and was filtered to remove salts and dried over anhydrous potassium carbonate. The solution was stripped under reduced pressure to yield the product 1h as a slightly yellow oil. (2.92 g, ~89%).

The following data (e.g., spectroscopic data) were obtained for the product 1h:

$^1$H NMR (CDCl$_3$) δ: 2.51 (s, 8H, C$\underline{H}_2$NH$_2$), 1.22 (q, J=8 Hz, 4H, C$\underline{H}_2$CH$_3$), 1.17-1.20 (m, 8H, CH$_2$s), 1.00 (br s, 8H, NH$_2$), 0.79 (t, J=8 Hz, 6H, CH$_2$C$\underline{H}_3$), 0.49 (m, 4H, CH$_2$Si), 0.03 (s, 12H, CH$_3$—Si)

$^{13}$C {$^1$H}NMR (CDCl$_3$): 45.65, 40.61, 36.23, 24.53, 19.42, 16.58, 7.42, 0.46. FT-IR: 3377, 3298, 2957, 2926, 2865, 1606, 1462, 1252, 1062, 840, 802, 723 cm$^{-1}$.

Exact mass MS: Calc'd for: C$_{20}$H$_{51}$N$_4$OSi$_2$ (M+H$^+$); 419.3601. Found; 419.3596.

Example 8

Preparation of Aminosiloxane Oligomer 1g

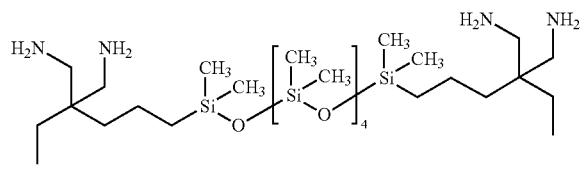

Aminosiloxane 1h (2.5 g, 5.97 mmol) was combined with octamethylcyclotetrasiloxane (1.77 g, 5.97 mmols of dimethylsiloxy groups) and 40 mg of tetramethylammonium hydroxide pentahydrate. The reaction mixture was heated to 85° C. to 90° C. under house vacuum. The vacuum was broken with nitrogen when the required temperature was reached. The reaction mixture was allowed to stir for about 5 hours, following which the temperature was increased to decompose the catalyst. When the temperature reached approximately 130° C., a moderate vacuum was applied. Heating was continued up to a temperature of 165° C., and the volatile catalyst decomposition by-products were distilled off. At this point, the reaction mixture was cooled to room temperature and filtered through a small amount of Celite 545 to remove some haziness. The product 1g was obtained as a light yellow oil (3.86 g, 90%).

The following data (e.g., spectroscopic data) were obtained for the product 1g:

$^1$H NMR (CDCl$_3$) δ: 2.50 (s, 8H, C$\underline{H}_2$NH$_2$), 1.14-1.26 (m, 12H, CH$_2$s), 0.93 (br s, 8H, NH$_2$), 0.78 (t, J=8 Hz, 6H, CH$_2$C$\underline{H}_3$), 0.50 (m, 4H, CH$_2$Si), 0.0-0.08 (series of singlets, 38H, CH$_3$—Si).

Example 9

Reaction of Amino-Siloxane Ia with Carbon Dioxide

To a tared, 25 mL, three-neck, round-bottom flask equipped with a mechanical stirrer, gas inlet and a gas outlet, and heated with a temperature controlled oil bath, was charged 0.5825 g of 1,3-bis(2,2-bis(aminomethyl)butyl)-1,1,3,3-tetramethyldisiloxane Ia. Dry CO$_2$ gas was introduced at a rate of ~50 mL/min into the flask, via a glass tube positioned approximately 10 mm above the surface of the stirred liquid. Contacting with CO$_2$ was continued for 2 hours at 40° C., after which time the exterior of the flask was cleaned and the flask weighed. The total weight gain of 0.0280 g corresponded to 19.8% of the theoretical amount of weight that should have been gained if all the amine groups had reacted with CO$_2$ (i.e. if the degree of reaction had been 100%). The reaction product was also a solid, and constitutes the reaction product of amino-siloxane Ia with carbon dioxide.

Example 10

Reaction of Triethylene Glycol and Amino-Siloxane Ia with Carbon Dioxide

To a tared, 25 mL, three-neck, round-bottom flask equipped with a mechanical stirrer, gas inlet and a gas outlet, and heated with a temperature controlled oil bath, was charged 0.5768 g of 1,3-bis(2,2-bis(aminomethyl)butyl)-1,1,3,3-tetramethyldisiloxane Ia and 0.5946 g of triethylene glycol (TEG). Dry CO$_2$ gas was introduced at a rate of ~50 mL/min into the flask, via a glass tube positioned approximately 10 mm above the surface of the stirred liquid. Contacting with CO$_2$ was continued for 2 hours at 40° C., after which time the exterior of the flask was cleaned, and the flask weighed. The total weight gain of 0.0831 g corresponded to 59.4% of the theoretical amount of weight that should have been gained if all the amine groups had reacted with CO$_2$ (i.e. if the degree of reaction had been 100%). The reaction product was a viscous liquid, and constitutes the reaction product of amino-siloxane Ia with carbon dioxide.

Example 11

Reaction of Amino-Siloxane 2b with Carbon Dioxide

To a tared, 25 mL, three-neck, round-bottom flask equipped with a mechanical stirrer, gas inlet and a gas outlet, and heated with a temperature controlled oil bath, was charged 0.8380 g of 2,2,6,6-tetramethyl-1,2,6-oxadisilinane-4-4-diyl)dimethanamine. Dry CO$_2$ gas was introduced at a rate of ~50 mL/min into the flask via a glass tube positioned approximately 10 mm above the surface of the stirred liquid. Contacting with CO$_2$ was continued for 2 hours at 40° C., after which time the exterior of the flask was cleaned and the flask weighed. The total weight gain of 0.1374 g corresponded to 86.5% of the theoretical amount of weight that should have been gained if all the amine groups had reacted with CO$_2$ (i.e. if the degree of reaction had been 100%). The reaction product was also a solid and constitutes the reaction product of amino-siloxane 2b with carbon dioxide.

Example 12

Reaction of TEG and Amino-Siloxane 2b with Carbon Dioxide

To a tared, 25 mL, three-neck, round-bottom flask equipped with a mechanical stirrer, gas inlet and a gas outlet, and heated with a temperature controlled oil bath, was charged 0.7822 g of 2,2,6,6-tetramethyl-1,2,6-oxadisilinane-4-4-diyl)dimethanamine 2b and 0.8059 g of triethylene glycol (TEG). Dry CO$_2$ gas was introduced at a rate of ~50 mL/min into the flask via a glass tube positioned approximately 10 mm above the surface of the stirred liquid. Contacting with CO$_2$ was continued for 2 hours at 40° C., after which time the exterior of the flask was cleaned and the flask weighed. The total weight gain of 0.0892 g corresponded to 60.2% of the theoretical amount of weight that should have been gained if all the amine groups had reacted with CO$_2$ (i.e. if the degree of reaction had been 100%). The reaction product was a viscous liquid and constitutes the reaction product of amino-siloxane 2b with carbon dioxide.

Example 13

Reaction of Amino-Siloxane 1h with Carbon Dioxide

To a tared, 25 mL, three-neck, round-bottom flask equipped with a mechanical stirrer, gas inlet and a gas outlet and heated with a temperature controlled oil bath, was charged 1.4949 g of aminosiloxane 1h. Dry CO$_2$ gas was introduced at a rate of ~50 mL/min into the flask via a glass tube positioned approximately 10 mm above the surface of the stirred liquid. Contacting with CO$_2$ was continued for 2 hours at 40° C., after which time the exterior of the flask was cleaned and the flask weighed. The total weight gain of 0.2003 g corresponded to 64% of the theoretical amount of weight that should have been gained if all the amine groups had reacted with CO$_2$ (i.e. if the degree of reaction had been 100%). The reaction product was a powdery solid, and constitutes the reaction product of amino-siloxane 1h with carbon dioxide.

Example 14

Reaction of Amino-Siloxane 1h with Carbon Dioxide in Triethylene Glycol

To a tared, 25 mL, three-neck, round-bottom flask equipped with a mechanical stirrer, gas inlet and a gas outlet and heated with a temperature controlled oil bath, was charged 0.8060 g of aminosiloxane 1h and 0.8196 g TEG. Dry CO$_2$ gas was introduced at a rate of ~50 mL/min into the flask via a glass tube positioned approximately 10 mm above the surface of the stirred liquid. Contacting with CO$_2$ was continued for 2 hours at 40° C., after which time the exterior of the flask was cleaned and the flask weighed. The total weight gain of 0.1615 g corresponded to 95% of the theoretical amount of weight that should have been gained if all the amine groups had reacted with CO$_2$ (i.e. if the degree of reaction had been 100%). The reaction product was a soft waxy material and constitutes the reaction product of amino-siloxane 1h with carbon dioxide.

Reaction of Amino-Siloxane Oligomer 1g with Carbon Dioxide

To a tared, 25 mL, three-neck, round-bottom flask equipped with a mechanical stirrer, gas inlet and a gas outlet and heated with a temperature controlled oil bath, was charged 2.0208 g of aminosiloxane oligomer 1g. Dry $CO_2$ gas was introduced at a rate of ~50 mL/min into the flask via a glass tube positioned approximately 10 mm above the surface of the stirred liquid. Contacting with $CO_2$ was continued for 2 hours at 40° C., after which time the exterior of the flask was cleaned, and the flask weighed. The total weight gain of 0.2047 g corresponded to 82% of the theoretical amount of weight that should have been gained if all the amine groups had reacted with $CO_2$ (i.e. if the degree of reaction had been 100%). The reaction product was a powdery solid and constitutes the reaction product of amino-siloxane oligomer 1g with carbon dioxide.

This written description uses examples to disclose some embodiments of the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of reducing the amount of carbon dioxide in a process stream, comprising the step of contacting the stream with a carbon dioxide absorbent comprising at least one amino-siloxane compound selected from the group consisting of amino-siloxanes having structure I and amino-siloxanes having structure III,

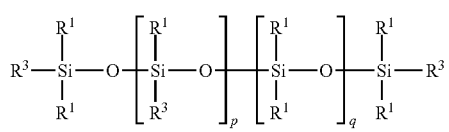
(I)

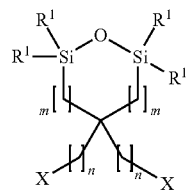
(III)

wherein $R^1$ is independently at each occurrence $C_1$-$C_5$ alkyl; $R^3$ is independently at each occurrence $R^1$ or $R^4$, wherein $R^4$ comprises structure II

(II)

and wherein $R^2$ is independently at each occurrence hydrogen or a $C_1$-$C_{10}$ aliphatic radical; X is independently at each occurrence a $NH_2$ group or a cyano group; m is independently at each occurrence an integer from 1-5; n is independently at each occurrence an integer from 0-5; p is an integer from 0-100; and q is an integer from 0-500; with the proviso that at least one of $R^3$ is $R^4$.

2. The method according to claim 1, wherein the amino-siloxane is a liquid.

3. The method according to claim 1, wherein said process stream is at least one selected from the group consisting of a combustion process, a gasification process, a landfill, a furnace, a steam generator, and a boiler.

4. The method according to claim 1, wherein said process stream is a fuel stream.

5. The method according to claim 4, wherein said fuel stream comprises natural gas.

6. The method according to claim 4, wherein said fuel stream comprises syn gas.

* * * * *